(12) United States Patent
Oike et al.

(10) Patent No.: US 8,110,613 B2
(45) Date of Patent: Feb. 7, 2012

(54) PROCESS FOR PRODUCING SILICON COMPOUND HAVING OXETANYL GROUP

(75) Inventors: Sayaka Oike, Tsukuba (JP); Akinori Kitamura, Tsukuba (JP); Hiroshi Suzuki, Minato-ku (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 13/128,308

(22) PCT Filed: Dec. 14, 2009

(86) PCT No.: PCT/JP2009/070845

§ 371 (c)(1),
(2), (4) Date: Jun. 23, 2011

(87) PCT Pub. No.: WO2010/073933

PCT Pub. Date: Jul. 1, 2010

(65) Prior Publication Data

US 2011/0245448 A1    Oct. 6, 2011

(30) Foreign Application Priority Data

Dec. 26, 2008    (JP) ................................ 2008-332075

(51) Int. Cl.
*C08G 65/18*    (2006.01)
*C07D 305/06*    (2006.01)

(52) U.S. Cl. ...................................... 522/168; 549/214

(58) Field of Classification Search ........................ None
See application file for complete search history.

(56) References Cited

U.S. PATENT DOCUMENTS

| | | | | |
|---|---|---|---|---|
| 5,463,084 A | * | 10/1995 | Crivello et al. | ............... 549/214 |
| 6,096,903 A | * | 8/2000 | Moszner et al. | ............. 549/214 |
| 6,121,342 A | * | 9/2000 | Suzuki et al. | ................ 522/148 |
| 6,624,236 B1 | * | 9/2003 | Bissinger et al. | ............. 524/588 |
| 6,743,510 B2 | * | 6/2004 | Ochiai | ........................... 428/413 |
| 6,852,822 B1 | * | 2/2005 | Bissigner et al. | ............... 528/32 |
| 2004/0197698 A1 | * | 10/2004 | Tamaki et al. | ............. 430/270.1 |
| 2005/0100772 A1 | * | 5/2005 | Ono | ............................... 429/33 |
| 2006/0132539 A1 | * | 6/2006 | Hino et al. | ...................... 347/47 |
| 2007/0055034 A1 | | 3/2007 | Tajima et al. | |
| 2007/0248828 A1 | * | 10/2007 | Yoneyama et al. | ........... 428/421 |
| 2008/0033137 A1 | * | 2/2008 | Tauchi et al. | ................... 528/27 |
| 2008/0293875 A1 | * | 11/2008 | Hatanaka | ...................... 524/588 |
| 2009/0087573 A1 | * | 4/2009 | Saito et al. | ................. 427/421.1 |

FOREIGN PATENT DOCUMENTS

JP    11-29640    2/1999
JP    11-199673    7/1999
WO    WO 2004/076534 A1    9/2004

* cited by examiner

*Primary Examiner* — Robert Loewe

(74) *Attorney, Agent, or Firm* — Oblon, Spivak, McClelland, Maier & Neustadt, L.L.P.

(57) ABSTRACT

Provided is a method for efficiently producing a cationically curable condensed silicon compound. There was an unsolved problem that, in a condensation reaction, an oxetanyl group is subjected to ring-opening under an acidic condition, while gelation is easily caused under an alkaline condition. It was found that a silicon compound (C) having an oxetanyl group can be obtained without causing gelation even at a high concentration by the present method including a first step of separately subjecting a silicon compound (A) having four siloxane bond-forming groups and a silicon compound (B) having an oxetanyl group to alcohol exchange reaction with 1-propanol and a second step of subjecting silicon compounds (AP) and (BP) undergone the first step to hydrolytic copolycondensation under an alkaline condition at a specific ratio.

11 Claims, No Drawings

PROCESS FOR PRODUCING SILICON COMPOUND HAVING OXETANYL GROUP

TECHNICAL FIELD

The present invention relates to a method for producing a silicon compound having an oxetanyl group. More specifically, the present invention relates to a method capable of producing the silicon compound at a high concentration without causing gelation, the silicon compound having a composition which can cause gelation during reaction under a prior art production method.

BACKGROUND ART

In hydrolytic copolycondensation of a silicon compound having a hydrolyzable group, acidic and alkaline conditions have a catalytic function. It has been known since old times that the condensation has different chemical mechanisms under acidic or alkaline conditions. For example Non-patent Document 1 discloses that tetraethoxysilane, which is a silicon compound of $SiX_4$ form, is hydrolyzed by an acid or alkali catalyst, whereas monomethyltriethoxysilane of $RSiX_3$ form causes reaction in the presence of an acid catalyst, but is unreactive in the presence of an alkali catalyst.

Patent Document 1 discloses that an acid catalyst opens the ring of an oxetanyl group, and that a method for producing a condensed silicon compound having an oxetanyl group, through the hydrolytic polycondensation of a silicon compound having an oxetanyl group and three hydrolyzable groups under an alkaline condition.

Patent Document 2 discloses that a silicon compound having an oxetanyl group and three hydrolyzable groups can be hydrolyzed and cocondensed with a reactive silicone having one or more siloxane bond-forming groups in one molecule thereof under an alkaline condition, and that the cured product of the condensate exhibits high contamination resistance owing to the effect of the silicone chain.

On the other hand, Patent Document 3 discloses a method for producing a condensed silicon compound having an oxetanyl group through the hydrolytic polycondensation of a silicon compound having an oxetanyl group and three hydrolyzable groups in the presence of an acid catalyst. The cured film of the condensed silicon compound obtained by the method showed markedly better result in a pencil hardness test in comparison with a silicone-containing cured film disclosed in Example of Patent Document 2, and thus is suitable for applications requiring surface hardness.

However, Patent Document 3 discloses that in Comparative Example 1 gelation occurred during the hydrolytic copolycondensation of a silicon compound having an oxetanyl group and three hydrolyzable groups, and a silicon compound having three siloxane bond-forming groups under an alkaline condition. It suggests that the possibility of gelation caused by the hydrolytic polycondensation of a silicon compound having an oxetanyl group and three hydrolyzable groups under an alkaline condition.

In Patent Document 3, cocondensation of a silicon compound having four siloxane bond-forming groups and a silicon compound having three hydrolyzable groups in the presence of an acid catalyst is specifically described in Example 8. The evaluation of the cured product of the silicon compound obtained by hydrolytic copolycondensation was not so different from that obtained using a silicon compound having three siloxane bond-forming groups. In summary, regarding the cocondensation of a silicon compound having an oxetanyl group and three hydrolyzable groups and a silicon compound having four siloxane bond-forming groups under an alkaline condition, there are known documents suggesting the possibility of gelation and no expectation for any special effect.

PRIOR ART DOCUMENTS

Patent Document

Patent Document 1: JP-A H11-029640
Patent Document 2: JP-A H11-199673
Patent Document 3: WO 2004/076534

Non-Patent Document

Non-Patent Document 1: "Sol-gel method and organic-inorganic hybrid materials" p. 42 (2007.8.31) by TECHNICAL INFORMATION INSTITUTE CO., LTD.

SUMMARY OF THE INVENTION

Problems that the Invention is to Solve

The prior art had problems that the ring of the oxetanyl group is opened upon condensation in the presence of an acid catalyst, whereas gelation tends to occur in the presence of an alkali catalyst, and that no special effect is achieved even if a silicon compound having four siloxane bond-forming groups is cocondensed to obtain a cured product having a high surface hardness.

The present invention is intended to provide a method for producing a silicon compound having an oxetanyl group at a high concentration without causing gelation during reaction, the silicon compound capable of leading to a cured product having a high surface hardness.

Means for Solving the Problems

The present inventors found that a silicon compound (C) having an oxetanyl group could be produced without causing gelation through a production method including a first process in which a silicon compound (A) having four siloxane bond-forming groups and a silicon compound (B) having an oxetanyl group were separately subjected to alcohol exchange reaction in 1-propanol, and a second process in which the resultant silicon compounds (AP) and (BP) after the first process were subjected to hydrolytic copolycondensation at a specific ratio under an alkaline condition, to accomplish the present invention.

Effect of the Invention

According to the present invention, a silicon compound (C) is produced from low-cost ingredients without causing gelation, through copolycondensation of a silicon compound (B) having an oxetanyl group to impart cationic curability and a silicon compound (A) having four siloxane bond-forming groups to increase the surface hardness of the cured product. The silicon compound (C) thus obtained is solvent-soluble and is readily adaptable to various applications.

The silicon compound (C) obtained by the production method of the present invention is solvent-soluble and exhibits good stability without causing thickening or gelation during storage. In addition, the production method of the present invention rarely causes gelation during reaction, in spite of the high initial concentrations.

The good storage stability of the silicon compound (C) is mainly due to the second process using an alkali catalyst. The hydrolysis reaction under an acidic condition in the production of a silicon compound tends to be insufficient, and thus the content ratio of unreacted alkoxy groups may be increased in comparison with the case of hydrolysis under an alkaline condition. Accordingly, the silicon compound produced through the hydrolytic copolycondensation under an acidic condition contains a siloxane bond-forming group such as an unreacted alkoxy group, and the unreacted groups may be gradually crosslinked during storage to cause problems such as viscosity increase and gelation. Since the present invention is characterized in that the second process requires an alkali catalyst, and an unreacted siloxane bond-forming group is difficult to be left, the silicon compound (C) obtained exhibits good storage stability, and rarely causes viscosity increase and gelation during long-term storage.

Hydrolysis reaction readily proceeds under an alkaline condition, but tends to cause a gel during condensation during reaction. The reason for this is that a curable silicon-containing compound produced using a silicon compound having four siloxane bond-forming groups (referred to as "Q monomer") is excellent in curability, and the cured product thereof has a high surface hardness, but if the Q monomer is subjected to hydrolytic copolycondensation under an alkaline condition, the condensation reaction of the Q monomer preferentially proceeds, and a network composed mainly of only the Q monomer is formed to cause a gel during reaction.

The decrease in the concentration of the reactant is generally effective for the prevention of gelation during reaction. However, synthesis at a low concentration is inefficient and uneconomical, because the yield is so low even if a large reaction vessel is used. In addition, the use of a large amount of solvent is uneconomical, and puts a heavy load on the environment.

On the other hand, a reaction at a high concentration is efficient and economical, but may increase the probability of contact between reactive silane molecules, and progress the intermolecular reaction to cause gelation.

The first process according to the present invention is one in which a silicon compound (A) having four siloxane bond-forming groups and a silicon compound (B) having an oxetanyl group are subjected to alcohol exchange reaction in 1-propanol. The alcohol exchange reaction improves a reactivity balance between the siloxane bond-forming group in the silicon compound (A) which quickly reacts and the hydrolyzable group in the silicon compound (B) which slowly reacts and is less likely to be captured in the cocondensate, whereby the formation of a gel during the reaction is prevented, and thus gelation hardly occurs during the reaction at a high concentration. In other words, under an alkaline condition, the condensation reaction of the Q monomer which rapidly reacts preferentially proceeds, however, the alcohol exchange reaction with 1-propanol of the siloxane bond-forming group which reacts too fast is conducted as fast as the reaction rate in the first process, and the alcohol exchange reaction with 1-propanol of the hydrolysable group which reacts slowly is conducted as slow as the reaction rate. In the hydrolytic copolycondensation according to the second process, the silicon compounds A and B change ones capable of reacting properly. Therefore, they can be subjected to copolycondensation without generating gel at high concentration. The present production method is based on the principle and allows efficient production through high concentration preparation.

According to the principle, it goes without saying that the production method including the alcohol exchange reaction according to the present invention is more excellent in the performance than the case wherein the siloxane bond-forming group in the silicon compound (A) and the hydrolysable group in the silicon compound (B) are all 1-propoxy groups. In the case of producing the silicon compounds (A) and (B), since 1-propanol is inferior in reactivity and 1-propoxy compounds are industrially expensive and difficult to obtain, the present invention is economically excellent considering this.

EMBODIMENTS FOR CARRYING OUT THE INVENTION

Hereinafter, the present invention is described in detail.

The production method of a silicon compound (C) of the present invention is characterized by comprising a first process in which a silicon compound (A) represented by the general formula (1) and a silicon compound (B) represented by the general formula (2) are subjected to alcohol exchange reaction in 1-propanol, and a second process in which the resultant composition is subjected to hydrolytic copolycondensation under an alkaline condition.

Silicon Compound (C)>

The silicon compound (C) is formed by the hydrolytic copolycondensation of the silicon compound (A), a silicon compound generated from the silicon compound (A) in the first process (referred to as "AP"), the silicon compound (B), and a silicon compound generated from the silicon compound (B) in the first process (referred to as "BP"). In the below-described second process, the siloxane bond-forming groups, hydrolyzable groups, and n-propoxy groups contained in A, B, AP and BP are mostly converted to siloxane bonds, so that the silicon compound (C) can be regarded as a polysiloxane composed of three-dimensional siloxane bonds (Si—O—Si) formed by hydrolysis of siloxane bond-forming groups, hydrolyzable groups, and n-propoxy groups.

The silicon compound (C) has an organic moiety containing a carbon atom and an inorganic moiety containing no carbon atoms. $R^0$ and R in the formula (2) representing the silicon compound (B) constitute the organic moiety. When a part of the hydrolyzable group such as an alkoxy group derived from the silicon compound (A), silicon compound (AP), silicon compound (B) and silicon compound (BP), is remained, the residue constitutes the organic moiety. The moiety other than the organic moiety is the inorganic moiety including no carbon atoms.

The silicon compound (C) has an oxetanyl group, and thus exhibits cationic curability. When the silicon compound (C) is subjected to cationic curing, a cured film can be obtained having a high surface hardness and high wear resistance.

In the case where a compound wherein n is 0 in the general formula (2), which is a T monomer having three hydrolyzable groups, is used as the silicon compound (B), when the compound, silicon compound (AP) and silicon compound (A) that are Q monomers having four siloxane bond-forming groups, are subjected to hydrolytic copolycondensation, the resultant silicon compound (C) has T and Q monomer units as structural units.

In such a case, the organosilicon compound (C) is allowed to have a structure in a partially laddered, caged, or randomized shape.

In the silicon compound (C), the hydrolyzable groups of the silicon compound (AP) and/or silicon compound (A) (in the present invention, the siloxane bond-forming group including a silanol group are referred to as "hydrolyzable groups") and hydrolyzable groups of the silicon compound (BP) and/or silicon compound (B) are condensed at the rate of preferably 92% or more by mol, more preferably 95% or more by mol, and further preferably 98% or more by mol. It is particularly preferred that substantially all the hydrolyzable groups be condensed. If the proportion of the residual hydrolyzable group is more than 8% by mol based on the hydrolyzable groups contained in the ingredients, the proportion of the inorganic moiety is lower than that in the intended structure, that is to say, polysiloxane structure is insufficiently formed, so that the resultant film may have insufficient hardness. In addition, the silicon compound (C) may have poor storage stability.

Further, the residual alkoxy group contain preferably 50% or more by mol, more preferably 70% or more by mol, and further preferably 90% or more by mol, of an alkoxy group having 3 or more carbon atoms, such as a propoxy group. Methoxy and ethoxy groups having 2 or less carbon atoms are highly reactive, and thus likely cause crosslinking reaction during storage to deteriorate storage stability.

The remaining ratio of the siloxane bond-forming group (including a hydrolyzable group) can be calculated from a spectrum of $^1$H NMR (nuclear magnetic resonance). The fact that "all the hydrolyzable groups have been substantially condensed" can be confirmed by a fact that peaks based on siloxane-bond forming groups are rarely observed in the $^1$H NMR spectrum for the obtained silicon compound (C) which is a polysiloxane compound.

<Silicon Compound (A)>

The silicon compound (A) according to the present invention is a compound which is represented by the following formula (1).

(In the formula (1), X is a siloxane bond-forming group, and Xs may be the same or different from each other.)

The silicon compound (A) is a compound having four Xs which are siloxane bond-forming groups (which may be referred to as "Q monomer"). The siloxane bond-forming group forms a siloxane bond upon reaction with a hydrolyzable group in the silicon compound (B). The resultant silicon compound (C) contains more inorganic content ratio depending on a component such as Si and O in comparison with the case of condensation of a silicon compound having one or more organic groups, and thus more strongly exhibits inorganic properties such as heat resistance and hardness. Therefore, the Q monomer can be regarded as an ingredient which increases the inorganic moiety of the condensate to be obtained.

The siloxane bond-forming group X in the general formula (1) represents a hydroxyl group (may be referred to as "silanol group") or a hydrolyzable group. The silicon compound (A) is not particularly limited so long as four siloxane bond-forming groups are bonded to a silicon atom. The plurality of Xs may be the same or different from each other. The hydrolyzable group may be any group having hydrolyzability, and example thereof includes a hydrogen atom, an alkoxy group, a cycloalkoxy group, an aryloxy group, arylalkoxy group, and the like.

Examples of the alkoxy group include methoxy group, ethoxy group, n-propoxy group, iso-propoxy group, n-butoxy group, iso-butoxy group, sec-butoxy group, tert-butoxy group, n-pentyloxy group, n-hexyloxy group and the like.

Examples the cycloalkoxy group include cyclopentyloxy group, cyclohexyloxy group and the like. Examples of the aralkyloxy group include benzyloxy group, 2-phenylethyloxy group and the like. Examples the aryloxy group include phenyloxy group, o-toluoyloxy group, m-toluoyloxy group, p-toluoyloxy group, naphtyloxy group and the like. Among these, an alkoxy group is preferable since it is excellent in hydrolyzability. An alkoxy group having 1 to 3 carbon atoms is more preferable. A methoxy group is further preferable, because the source material thereof is readily available, inexpensive, and easy to control a hydrolysis reaction therefor. These compounds may be used singly or in combination of two or more types thereof. The silicon compound (A) is preferably a tetramethoxysilane, tetraethoxysilane, and tetra n-propoxysilane. In addition, the tetramethoxysilane is more preferable because it is readily available. At least a part of the siloxane bond-forming group is converted to a n-propoxy group by the below-described alcohol exchange reaction.

<Silicon Compound (B)>

The silicon compound (B) according to the present invention has an organic group containing an oxetanyl group. The compound is an ingredient for imparting cationic curability to the silicon compound (C) which is obtained by the present production method, and is represented by the following general formula (2).

(In the formula (2), $R^0$ is an organic group having an oxetanyl group, $R^0$s may be the same or different from each other, R is an alkyl group having 1 to 6 carbon atoms, an aralkyl group having 7 to 10 carbon atoms, an aryl group having 6 to 10 carbon atoms, or an organic group having an oxetanyl group, Rs may be the same or different from each other, Y is a hydrolyzable group, Ys may be the same or different from each other, and n is 0 or 1.)

$R^0$ is an organic group containing an oxetanyl group, and the organic group preferably has 20 or less carbon atoms. When $R^0$ has 20 or less carbon atoms, good and stable cationic curability are imparted to the silicon compound (C) which is obtained by the present production method. An organic group having a structure represented by the following general formula (3) is preferable as $R^0$. When the number of the carbon atoms in $R^3$ is small in the general formula (3), the resultant silicon compound (C) has a large proportion of the inorganic moiety, and the cured product likely has a high surface hardness, being favorable. $R^3$ is preferably a hydrogen atom or an alkyl group having 1 to 6 carbon atoms, and more preferably an ethyl group.

When the number of the carbon atoms in $R^4$ is small in the general formula (3), the resultant silicon compound (C) has a large proportion of the inorganic moiety, and the cured product likely has a high surface hardness, being favorable. $R^4$ is preferably an alkylene group having 2 to 6 carbon atoms, and more preferably a propylene group (trimethylene group). The reason is that the compounds forming such organic functional groups are industrially readily available or easy to synthesize.

A compound in which n is zero has three hydrolyzable groups, and may be referred to as "T monomer". A compound in which n is 1 has two hydrolyzable groups, and may be referred to as "D monomer". For increasing the proportion of the inorganic moiety in the resultant silicon compound (C), n is preferably zero. Additionally, for improving solubility of the silicon compound (C) in a solvent, n is preferably 1.

Further, from the viewpoint of a balance between the proportion of the inorganic moiety and solubility in a solvent, a silicon compound wherein n is zero and a silicon compound wherein n is 1 may be used in combination. In this case, the ratio between the silicon compound wherein n is zero and the silicon compound wherein n is 1 is appropriately selected according to the intended use of the resultant silicon compound (C). The average value of n is preferably from 0 to 0.5, and more preferably from 0 to 0.3.

Y in the general formula (2) is a hydrolyzable group and is not limited so long as it is a hydrolyzable group. Example thereof includes a hydrogen atom, an alkoxy group, a cycloalkoxy group, an aryloxy group, an arylalkoxy group, and the like. Examples of the alkoxy group include methoxy group, ethoxy group, n-propoxy group, iso-propoxy group, n-butoxy group, iso-butoxy group, sec-butoxy group, tert-butoxy group, n-pentyloxy group, n-hexyloxy group and the like. Examples the cycloalkoxy group include cyclopentyloxy group, cyclohexyloxy group and the like. Examples of the aralkyloxy group include benzyloxy group, 2-phenylethyloxy group and the like. Examples the aryloxy group include phenyloxy group, o-toluoyloxy group, m-toluoyloxy group, p-toluoyloxy group, naphtyloxy group and the like. Among these, an alkoxy group is preferable since it is excellent in hydrolyzability. An alkoxy group having 1 to 3 carbon atoms is more preferable. A methoxy group is further preferable, because the source material thereof is readily available, inexpensive, and easy to control a hydrolysis reaction therefor. These groups may be bonded singly or in combination of two or more types thereof.

Among these, an alkoxy group, cycloalkyxy group and aryloxy group are preferable as Y. More preferable is an alkoxy group, and specified example includes a methoxy group, ethoxy group and n-propoxy group. Among them, a methoxy group is preferred because it is industrially readily available and easy to synthesis. At least a part of Y is converted to a n-propoxy group by the below-described alcohol exchange reaction.

The silicon monomer having only one siloxane bond-forming group may be referred to as "M monomer". The M monomer has three organic groups, and gives a condensate having a lower proportion of inorganic moiety than that obtained using Q, T, or D monomer. A method for avoiding gelation during reaction is known which is configured to cause the M monomer such as trimethylalkoxysilane and hexamethyldisiloxane, to act as an end capping agent. However, the addition of the M monomer prevents gelation, but decreases the inorganic moiety of the resultant condensate, and thus deteriorates the inorganic properties of the cured product, such as heat resistance and surface hardness. The present invention is characterized in that the T monomer and/or D monomer, and Q monomer are copolycondensed without causing gelation, in place of using the M monomer as an end capping agent.

The M monomer may be added at a low proportion without deteriorating the inorganic properties in the present invention. More specifically, the M monomer may be added to the reaction system for copolycondensation in an amount of $\frac{1}{10}$ mol or less with reference to the total mol number of the Q monomer and T monomer and/or D monomer. The composition obtained by the reaction is also included in the scope of the present invention.

<First Process>

The first process according to the present invention is a reaction process in which a silicon compound (A) represented by the above-described general formula (1) and a silicon compound (B) represented by the above-described general formula (2) are subjected to alcohol exchange reaction in 1-propanol. The silicon compound (A) to be used in the first process may be used singly or in combination of two or more types thereof. And the silicon compound (B) may be used singly or in combination of two or more types thereof.

In the first process, as a result of the alcohol exchange reaction between the siloxane bond-forming group in the silicon compound (A) and 1-propanol, the silicon compound (A) contains a n-propoxy group derived from 1-propanol.

In addition, as a result of the alcohol exchange reaction between the hydrolyzable group in the silicon compound (B) and 1-propanol, the silicon compound (B) contains a n-propoxy group derived from 1-propanol.

Through the first process, a reaction product of the organosilicon compound (A) having a n-propoxy group (hereinafter, referred to as "silicon compound (AP)"), and a reaction product of the organosilicon compound (B) having a n-propoxy group (hereinafter, referred to as "silicon compound (BP)") are produced, respectively.

The silicon compound (AP) is produced by exchanging at least one of the four siloxane bond-forming groups in the silicon compound (A) with n-propoxy group.

The silicon compound (BP) is produced by exchanging at least one of the two or three hydrolyzable groups in the silicon compound (B) with n-propoxy group.

The alcohol used in the first process is a 1-propanol. Since at least a part of the siloxane bond-forming groups in the silicon compound (A) is exchanged with a n-propoxy group, and at least a part of the hydrolyzable groups in the silicon compound (B) is exchanged with a n-propoxy group, these monomers can be copolycondensed with a good balance in the below-described second process. In the case where the siloxane bond-forming group in the silicon compound (A) is a methoxy group or ethoxy group which has high reactivity, only the Q monomer having high reactivity intrinsically may be condensed and crosslinked to form a network and cause gelation. The exchange with a n-propoxy group having moderate reactivity allows smooth and effective progress of the condensation reaction.

If 2-propanol or 1-butanol is used as the alcohol in the first process, the reaction product has a poorly reactive i-propoxy group or n-butoxy group, and may not be smoothly condensed with the compounds (AP) and (BP) obtained in the first process.

Additionally, if methanol or ethanol is used as the alcohol in the first process, the reaction product has a methoxy group or ethoxy group having relatively higher reactivity than the reaction product obtained using 1-propanol, so that the hydrolytic copolycondensation between the compounds (AP) and (BP) may not uniformly proceed, and a gel may be formed, or a compound having low stability may be obtained.

The reaction temperature in the first process is preferably in the range from 0° C. to 100° C., more preferably from 10° C. to 90° C., and further preferably from 20° C. to 80° C.

The reaction time is preferably in the range from 5 minutes to 30 hours, more preferably from 10 minutes to 24 hours, and further preferably from 15 minutes to 24 hours.

The pH condition in the first process may be alkaline, neutral or acidic, but is preferably alkaline, because the hydrolytic copolycondensation in the below-described second process are carried out under an alkaline condition.

When the first process is carried out under an alkaline condition, the pH of the reaction liquid is more than 7. In this case, the pH of the reaction liquid is preferably in the range from 8 to 13, and further preferably 9 or higher.

When the pH condition in the first process is set to alkaline condition, an alkaline agent is added. The alkaline agent acts as a reaction catalyst for smoothly performing alcohol exchange reactions between alkoxy groups in the silicon compound (A) and silicon compound (B), and 1-propanol.

Examples of the alkaline agent include ammonia, an organic amine, tetramethylammonium hydroxide, tetraethylammonium hydroxide, tetrapropylammonium hydroxide, tetrabutylammonium hydroxide, choline, sodium hydroxide, potassium hydroxide, calcium hydroxide and the like. Among these, an ammonium compound having a quaternary nitrogen atom leading an excellent catalytic activity is preferable, and tetramethylammonium hydroxide is more preferable since it is readily available. The alkali agent may be used singly or in combination of two or more types thereof.

The amount of the alkaline agent to be used is preferably in the range from 1 to 20 mol, and more preferably from 3 to 15 mol based on 100 mol of the total mol number of the silicon compound (A) and silicon compound (B). When the alkaline agent is used in an amount of 5 to 10 mol, the alcohol exchange reaction is efficiently progressed, being economically preferable.

<Second Process>

The second process is a process in which water is added to the resultant composition under an alkaline condition to perform the hydrolytic copolycondensation.

The composition obtained in the first process may be the same as the reaction solution after the first process. The composition contains a silicon compound (AP) and silicon compound (BP) each having a n-propoxy group formed by the alcohol exchange reaction.

Regarding usage ratio of the silicon compound (AP) and silicon compound (BP), the amount of the silicon compound (AP) is in the range from 0.3 to 2.8 mol, preferably from 0.8 to 2.5 mol, and further preferably from 1 to 2.3 mol based on 1 mol of the silicon compound (BP). When the amount of the silicon compound (AP) to be used is in the range from 0.3 to 2.8 mol based on 1 mol of the silicon compound (BP), the hydrolytic copolycondensation can be smoothly progressed to produce a silicon compound (C) efficiently without generating a gel. It is noted that the silicon compound (AP) and silicon compound (BP) may contain the silicon compound (A) and silicon compound (B), respectively, the usage ratio may be calculated according to the formulation ratio of the silicon compounds (A) and (B) in the first process, and that the expression of "amount of the silicon compound (A) to be used is in the range from 0.3 to 2.8 mol based on 1 mol of the silicon compound (B) before the first process" is essentially the same as one described above.

When the pH condition in the second process is set to alkaline condition, an alkaline agent is added to the reaction system. The alkaline agent acts as a reaction catalyst for smoothly performing hydrolysis of an alkoxy group which is a hydrolyzable group in the silicon compound (AP) and silicon compound (BP) obtained in the first process, and smooth hydrolytic copolycondensation of the silicon compound (AP) and silicon compound (BP).

Examples of the alkaline agent include ammonia, an organic amine, tetramethylammonium hydroxide, tetraethylammonium hydroxide, tetrapropylammonium hydroxide, tetrabutylammonium hydroxide, choline, sodium hydroxide, potassium hydroxide, calcium hydroxide and the like. Among these, an ammonium compound having a quaternary nitrogen atom leading an excellent catalytic activity is preferable, and tetramethylammonium hydroxide is more preferable since it is readily available. The alkali agent may be used singly or in combination of two or more types thereof.

The amount of the alkaline agent to be used in the second process is preferably in the range from 1 to 20 mol, more preferably from 3 to 15 mol, and further preferably from 5 to 10 mol based on 100 mol of the total mol number of the silicon compound (AP) and silicon compound (BP). When the alkaline agent is used in above amount, the hydrolytic copolycondensation is efficiently progressed, being economically preferable.

The second process is a process under an alkaline condition and the pH of the reaction liquid is exceeding 7. The pH is preferably in the range from 8 to 13, and more preferably from 9 to 13. Keeping the reaction system at such a pH enables to perform favorable hydrolytic copolycondensation.

If the reaction condition is acidic (less than pH 7), the resultant silicon compound by the hydrolytic copolycondensation may be inferior in storage stability and a gel may be generated during storage according to the reaction condition or the like.

Additionally, under a neutral condition (near pH 7), the hydrolytic copolycondensation is difficult to progress.

Therefore, when the organosilicon compound (AP) and the organosilicon compound (BP) are subjected to hydrolytic copolycondensation under an alkaline condition (more than pH 7), a silicon compound having high storage stability is obtained.

In the second process, an organic solvent can be used as a reaction solvent. Examples of the organic solvent include an alcohol such as methyl alcohol, ethyl alcohol, 1-propanol and 2-propanol; a ketone such as acetone and methyl ethyl ketone; tetrahydrofurane, toluene, 1,4-dioxane, hexane, ligroin, and the like. Among these, a solvent having higher polarity such as alcohol is preferable because of the excellent solubility of the silicon compound (C). The reaction solvent to be used is preferably a 1-propanol since 1 propanol is used in the first process and the resultant composition in the first process can be used in the second process. These solvents may be used singly or in combination of two or more types thereof.

In the second process, water is added for hydrolysis. The amount of the water is preferably in the range from 0.5 to 10 equivalents, and more preferably from 1 to 5 equivalents with reference to 1 equivalent of the alkoxy group. If the amount of the water is less than 0.5 equivalent, the reaction may be insufficiently achieved. On the other hand, if the amount of the water is more than 10 equivalents, the process of removing the water after the reaction is prolonged, which is uneconomical and may lead to a gel generation.

In the case where water is added in the second process, the water may be used alone, or a dilution with any appropriate organic solvent may be used dropwise. It is preferred that the water is diluted with any appropriate organic solvent. The reason for this is as follows. If water is added alone, the concentration of the water may be locally high at the dripped position and uniform reaction may not be progressed in the condition of the excessive water, and a gel generation may be caused.

Examples of the appropriate organic solvent include an alcohol such as methyl alcohol, ethyl alcohol and isopropyl alcohol, a ketone such as acetone and methyl ethyl ketone, an ether such as tetrahydrofurane and 1,4-dioxane, and the like. Two or more organic solvents may be used. Among these, an alcohol is preferred since it favorably dissolves the ingredients and product. It is more preferable that the solvent used as the reaction solvent be used for dilution, and that 1-propanol is most preferred.

If the initial total concentration of the silicon compounds (AP) and/or (A) and silicon compounds (BP) and/or (B) is too high in a reaction liquid according to the second process, gelation tends to occur, whereas too low concentrations are uneconomical. The concentration is preferably in the range from 1% to 60%, more preferably from 5% to 40%, and further preferably from 10% to 30% in terms of the concentration based on a weight of the silicon compound (C) to be obtained.

The higher the reaction temperature in the second process is, the faster the reaction proceeds. However, the reaction temperature is preferably lower thereby preventing side reactions. The reaction temperature is preferably in the range from 0° C. to 120° C., more preferably from 10° C. to 100° C., further preferably from 40° C. to 100° C., and particularly from 40° C. to 80° C. The reaction time for the second process is preferably in the range from 30 minutes to 30 hours, more preferably from 30 minutes to 10 hours, and further preferably from 1 to 8 hours.

<Other Process>

The present invention preferably include a neutralization process, volatile component removing process (1), dissolving process, washing process, and volatile component removing process (2) after the condensation process.

The neutralization process is a process in which an acid is added to the composition obtained in the second process to neutralize the alkaline agent used in the first and second processes. Examples of the acid include an inorganic acid such as phosphoric acid, nitric acid, sulfuric acid and hydrochloric acid, a carboxylic acid such as acetic acid, formic acid, lactic acid, acrylic acid and oxalic acid, a sulfonic acid such as p-toluenesulfonic acid and methanesulfonic acid, and the like. The amount of the acid to be used is preferably in the range from 1 to 1.1 equivalent, and more preferably from 1 to 1.05 equivalent relative to 1 equivalent of the alkaline agent.

The volatile component removing process (1) is a process in which a volatile component is removed from the intermediate product (that means "treated composition obtained after each process"; hereinafter the same) obtained in the neutralization process. In the volatile component removing process (1), distillation is conducted under a condition of ordinary pressure (atmospheric pressure) or reduced pressure. The volatile component to be removed is mainly an organic solvent used as the reaction solvent in the neutralization process. This process is preferably conducted when such an organic solvent is used, which is compatibly mixed with water, like methanol, because such a solvent is inconvenient for washing by water to be described later.

The volatile component removing process (1) and dissolving process to be described later can be omitted, in case that the organic solvent used as the reaction solvent is incompatible with water and is an organic solvent suitable for washing by water in the washing process, and in case that, although the organic solvent is one such as an alcohol, which compatibly mixes with water, washing process for the intermediate product can be conducted by adding a large amount of an organic solvent suitable for washing by water. Because of economical merit, the volatile component removing process (1) is preferably conducted.

The dissolving process is a process in which the intermediate product obtained in the volatile component removing process (1) is dissolved in an organic solvent for washing, and it is a preferable process in the present invention. As the organic solvent for washing, a compound is used which dissolves the organosilicon compound (C) as a reaction product therein and which is incompatible with water and leads to a good separation after the below-described washing process. The term "incompatible with water" implies that, when water and the organic solvent for washing are sufficiently mixed with each other and then the mixture is left to stand still, the mixture is separated into a water layer and an organic layer. The preferable organic solvent for washing is described in the explanation for the washing process.

The washing process is a process in which the intermediate product obtained in the dissolving process (the intermediate product obtained in the neutralization process when the volatile component removal process and dissolving process are omitted) is washed with water, and it is a preferable process in the present invention. According to the washing process using water, the alkaline agent used in the second process, the acid used in the neutralization process, and the salt thereof are substantially removed from the organic layer.

Examples of the organic solvent for washing (that is an organic solvent dissolving a material to be washed with water in the washing process) include a ketone such as methyl isobutyl ketone, an ether such as diisopropyl ether, an aromatic hydrocarbon such as toluene, a hydrocarbon such as hexane, an ester such as ethyl acetate and propylene glycol monomethyl ether acetate (hereinafter, referred to as "PGMEA"), and the like.

The washing process includes a step in which water and the intermediate product are subjected to mixing to contact the water and the intermediate product, and a step in which a water layer and an organic layer (intermediate product) are separated. When mixing of water and the intermediate product is insufficient, when contact of water and the intermediate product is insufficient, or when the separation of the organic layer (intermediate product) is insufficient, the resultant silicon compound (C) sometimes contains a large amount of impurities and is a silicon compound (C) having inferior stability.

The temperatures in the step for mixing and contacting water with the intermediate product and the step for separating the water layer and an organic layer (intermediate product) in the washing process are not particularly limited. Preferable temperature is in the range from 0° C. to 70° C., and more preferably from 10° C. to 60° C. Particularly preferable temperature is in the range from 40° C. to 60° C. from the viewpoint of a shortening effect of the separation time.

The volatile component removing process (2) is a process in which a volatile component is removed from the intermediate product obtained in the washing process, and it is a preferable process in the present invention. The distillation is conducted under a condition of ordinary pressure (atmospheric pressure) or reduced pressure in the volatile component removing process (2). The volatile component to be removed in the volatile component removing process (2) is mainly the organic solvent. If the other volatile components are contained, all are removed simultaneously.

It is noted that, when the silicon compound (C) is not isolated and the organic solvent for washing is used as a solvent for the silicon compound (C), the volatile component removal process (2) may be omitted.

EXAMPLE

Hereinafter, the present invention is specifically described using Examples. The present invention is not limited to these Examples. In the following description, "Mn" means number average molecular weight, "Mw" means weight average molecular weight, and they were calculated by gel permeation chromatographic method (hereinafter, referred to as "GPC") on the basis of the comparison of the retention time with the standard polystyrene molecular weight. The ratio Mw/Mn is usually a value named as "polydispersity index". It is understood that when all the molecules are identical, Mw/Mn is 1, and that Mw/Mn is regarded as an index which becomes larger as the molecular weight distribution increases.

[1] Production of Silicon Compound

Example 1

Preparation of Silicon Compound C1

1.1 kg (4.01 mol) of 3-ethyl-3-((3-(trimethoxysilyl)propoxy)methyl)oxetane represented by the following formula (4) (one of the monomers giving the T structural unit in the silicon compound (C) to be formed; hereinafter referred to as "TMSOX"), 1.1 kg (7.24 mol) of tetramethoxysilane (one of the monomers giving the Q structural unit; hereinafter referred to as "TMOS"), and 1.1 kg of 1-propanol were charged into a reaction vessel provided with a stirrer and a thermometer, and then 0.29 kg of a methanol solution of 25% by weight of tetramethylammonium hydroxide (containing 6.8 mol of methanol and 0.8 mol of tetramethylammonium hydroxide) was gradually added therein. After reaction was performed at a temperature of 60° C. for an hour, a mixture of 750 g (41 mol) of water and 750 g of 1-propanol was added dropwise over a period of 0.5 hour while the reaction liquid was stirred. The reaction was performed at 60° C. for 6 hours including the dropping time, and then nitric acid was added to the reaction liquid for neutralization. An organic solvent and water were evaporated under reduced pressure, and the residue was dissolved in PGMEA and washed with water to remove salts and excessive acids. The PGMEA solution obtained was subjected to evaporation under reduced pressure to remove the solvent, and thus obtaining a colorless solid (compound C1). The yield was 1.2 kg and the weight yield calculated from the initial amounts of the starting materials was 91%.

The compound C1 was subjected to $^1$H NMR analysis and IR (infrared absorption) to confirm a presence of an oxetanyl group.

$^1$H NMR analysis was conducted by precisely weighing and mixing 1 g of the compound C1 and 100 mg of hexamethyldisiloxane (hereinafter, referred to as "HMDSO") as an internal standard substance and determining based on a signal strength of the proton of HMDSO. The content of a structural unit (T monomer unit) derived from the silicon compound (AP), i.e., TMSOX, and the content of an alkoxy group in the silicon compound C1 were determined by $^1$H NMR analysis. Based on these contents, the content of a structural unit (Q monomer unit) derived from the silicon compound (BP), i.e., TMOS, was calculated. As a result, the obtained organosilicon compound C1 was confirmed to be a copolycondensate by stoichiometric reaction of the silicon compound (AP) and the silicon compound (BP).

The content of the alkoxy group (methoxy group bonded to a silicon atom) of the silicon compound C1 calculated from $^1$H NMR spectrum, was an amount corresponding to 0.8% based on the total amount of the alkoxy group contained in the starting materials.

Mn and Mw of the silicon compound thus obtained were 3,200 and 350,000, respectively, and no peak was observed in the polymer region corresponding to a retention time of 6 to 10 minutes. Mw/Mn was calculated as 108, and the ratio of inorganic moiety was 50% in the silicon compound C1.

The compound C1 obtained in Example 1 was dissolved in the same amount of PGMEA, and they were heated in an oil bath at a temperature of 60° C. to observe the appearance over time. Gelation was not occurred after lapse of 5 days, and the solution remained uniform.

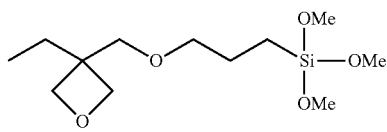

(4)

Example 2

Production of Silicon Compound C2

27.82 g (0.1 mol) of TMSOX represented by the following formula (4), 28.19 g (0.185 mol) of TMOS, and 111.5 g of 1-propanol were charged into a reaction vessel provided with a stirrer and a thermometer, and then 7.29 g of a methanol solution of 25% by weight of tetramethylammonium hydroxide (containing 0.17 mol of methanol and 20 mmol of tetramethylammonium hydroxide) was gradually added therein. After reaction was performed at a temperature of 60° C. for an hour, a mixture of 18.72 g (1.04 mol) of water and 20.0 g of 1-propanol was added dropwise over a period of 0.5 hour. The reaction was performed at 60° C. for 6 hours including the dropping time, and then nitric acid was added to the reaction liquid for neutralization. An organic solvent and water were evaporated under reduced pressure, the residue was dissolved in PGMEA, and washed with water thereby removing salts and excessive acids. The PGMEA solution obtained was subjected to evaporation under reduced pressure to remove the solvent, and thus obtaining a colorless solid (compound C2). The yield was 28.8 g and the weight yield was 90%.

The silicon compound C2 was subjected to $^1$H NMR analysis and IR analysis, to confirm a presence of an oxetanyl group.

This organosilicon compound C2 was also confirmed to be a copolycondensate by stoichiometric reaction of TMSOX and TMOS, based on the same $^1$H NMR analysis as that in Example 1.

The content of the alkoxy group (methoxy group bonded to a silicon atom) of the silicon compound C2 calculated from $^1$H NMR spectrum, was an amount corresponding to 0.9% based on the total amount of the alkoxy group contained in the starting materials.

In the silicon compound C2, the ratio of inorganic moiety was 50%.

Mn and Mw of the silicon compound thus obtained were 3,500 and 400,000, respectively, and no peak was observed in the polymer region corresponding to a retention time of 6 to 10 minutes. Mw/Mn was calculated as 114.

The compound C2 obtained in Example 2 was dissolved in the same amount of PGMEA, and they were heated in an oil bath at a temperature of 60° C. to observe the appearance over time. Gelation was not occurred after lapse of 5 days, and the solution remained uniform.

Example 3

Production of Silicon Compound C3)

27.82 g (0.1 mol) of TMSOX represented by the following formula (4), 28.19 g (0.185 mol) of TMOS, and 111.5 g of 1-propanol were charged into a reaction vessel provided with a stirrer and a thermometer, and then 7.29 g of a methanol solution of 25% by weight of tetramethylammonium hydroxide (containing 0.17 mol of methanol and 20 mmol of tetramethylammonium hydroxide) was gradually added therein. After reaction was performed at a temperature of 20° C. for an hour, a mixture of 18.72 g (1.04 mol) of water and 20.0 g of 1-propanol was added dropwise over a period of 0.5 hour. The reaction was performed at 20° C. for 6 hours including the dropping time, and then nitric acid was added to the reaction liquid for neutralization. An organic solvent and water were evaporated under reduced pressure, the residue was dissolved in PGMEA, and washed with water thereby removing salts and excessive acids. The PGMEA solution obtained was subjected to evaporation under reduced pressure to remove the solvent, and thus obtaining a colorless solid (compound C3). The yield was 27.2 g and the weight yield was 85%.

The compound C3 was subjected to $^1$H NMR analysis and IR analysis, to confirm a presence of an oxetanyl group.

This organosilicon compound C3 was also confirmed to be a copolycondensate by stoichiometric reaction of TMSOX and TMOS, based on the same $^1$H NMR analysis as that in Example 1.

The content of the alkoxy group (methoxy group bonded to a silicon atom) of the silicon compound C3 calculated from $^1$H NMR spectrum, was an amount corresponding to 2.0% based on the total amount of the alkoxy group contained in the starting materials.

In the silicon compound C3, the ratio of inorganic moiety was 50%.

Mn and Mw of the silicon compound thus obtained were 3,800 and 500,000, respectively, and no peak was observed in the polymer region corresponding to a retention time of 6 to 10 minutes. Mw/Mn was calculated as 132.

The compound C3 obtained in Example 3 was dissolved in the same amount of PGMEA, and they were heated in an oil bath at a temperature of 60° C. to observe the appearance over time. The viscosity slightly was increased after lapse of 5 days, however, gelation was not occurred and the solution remained uniform.

Comparative Example 1

39.2 g (0.14 mol) of TMSOX, 39.6 g (0.26 mol) of TMOS, and 39.3 g of methanol were charged into a reaction vessel provided with a stirrer and a thermometer, and then 10.4 g of a methanol solution of 25% by weight of tetramethylammonium hydroxide (containing 0.24 mol of methanol and 28 mmol of tetramethylammonium hydroxide) was gradually added therein. After reaction was performed at a temperature of 21° C. for an hour, a mixture of 26.3 g (1.46 mol) of water and 26.6 g of 1-propanol was added dropwise. Gelation occurred during the addition.

Comparative Example 2

27.73 g (0.1 mol) of TMSOX, 28.12 g (0.18 mol) of TMOS, and 27.57 g of methanol were charged into a reaction vessel provided with a stirrer and a thermometer, and then 7.41 g of a methanol solution of 25% by weight of tetramethylammonium hydroxide (containing 0.18 mol of methanol and 20 mmol of tetramethylammonium hydroxide) was gradually added therein. After reaction was performed at a temperature of 60° C. for an hour, a mixture of 18.9 g (1 mol) of water and 18.91 g of methanol was added. The reaction was performed at 60° C. for 6 hours, and then nitric acid was added to the reaction liquid for neutralization. An organic solvent and water were evaporated under reduced pressure, the residue was dissolved in PGMEA, and washed with water thereby removing salts and excessive acids.

The GPC of the organic layer during water washing was measured; a large peak was observed in the polymer region corresponding to a retention time of 6 to 10 minutes, indicating the presence of an abundance of polymer components having a molecular weight of more than 400,000, and implying poor stability. The measured data was in Table 1. Additionally, during water washing, separability between the water layer and organic layer was very poor, so that they were not clearly separated, which resulted in the fail to isolate the intended object.

Comparative Example 3

27.70 g (0.1 mol) of TMSOX, 28.5 g (0.185 mol) of TMOS, and 27.54 g of ethanol were charged into a reaction vessel provided with a stirrer and a thermometer, and then 7.3 g of a methanol solution of 25% by weight of tetramethylammonium hydroxide (containing 0.18 mol of methanol and 20 mmol of tetramethylammonium hydroxide) was gradually added therein. After reaction was performed at a temperature of 60° C. for an hour, 18.74 g (1 mol) of water and 18.7 g of ethanol were added dropwise. The reaction was performed at 60° C. for 6 hours, and then nitric acid was added to the reaction liquid for neutralization. An organic solvent and water were evaporated under reduced pressure, the residue was dissolved in PGMEA, and washed with water thereby removing salts and excessive acids. The PGMEA solution obtained was subjected to evaporation under reduced pressure to remove the solvent, and thus obtaining a pale yellow solid. The yield was 29.08 g and the weight yield was 91%.

The resultant compound was subjected to $^1$H NMR analysis and IR analysis, to confirm a presence of an oxetanyl group.

This organosilicon compound C4 was also confirmed to be a copolycondensate by stoichiometric reaction of the silicon compound (A) and silicon compound (B), based on the same $^1$H NMR analysis as that in Example 1.

The content of the alkoxy group (methoxy group bonded to a silicon atom) of the silicon compound C4 calculated from $^1$H NMR spectrum, was an amount corresponding to 2.6% based on the total amount of the alkoxy group contained in the starting materials.

Mn and Mw of the silicon compound thus obtained were calculated at 4,300 and 3,000,000, respectively. A large peak was observed in the polymer region corresponding to a retention time of 6 to 10 minutes. Since the region is one wherein Mw is more than 400,000 and which is hard to determine, the Mw is expressed as ">1000000" which means greater than 1000000, and the Mw/Mn is expressed as ">200" which means greater than 200 in Table 1.

The compound obtained in Comparative Example 3 was dissolved in the same amount of PGMEA, and they were heated in an oil bath at a temperature of 60° C. to observe the appearance over time. Gelation was occurred by the next day. It is found that stability is low when all the residual alkoxy groups are ethoxy groups.

Comparative Example 4

27.74 g (0.1 mol) of TMSOX, 28.20 g (0.185 mol) of TMOS, and 27.54 of 2-propanol were charged into a reaction vessel provided with a stirrer and a thermometer, and then 7.3 g of a methanol solution of 25% by weight of tetramethylammonium hydroxide (containing 0.18 mol of methanol and 20 mmol of tetramethylammonium hydroxide) was gradually added therein. After reaction was performed at a temperature of 60° C. for an hour, 18.87 g (1 mol) of water and 18.88 g of 2-propanol were added dropwise. The reaction was performed at 60° C. for 6 hours, and then nitric acid was added to the reaction liquid for neutralization. An organic solvent and water were evaporated under reduced pressure, the residue was dissolved in PGMEA, and washed with water thereby removing salts and excessive acids. The PGMEA solution obtained was subjected to evaporation under reduced pressure to remove the solvent, and thus obtaining a pale yellow solid. The yield was 28.73 g and the weight yield was 90%.

After the reaction, the reaction liquid immediately after neutralization with nitric acid was analyzed by gas chromatography. Peaks attributable to the silane monomer were found. On the other hand, when the solution after the reaction was analyzed by GPC, Mn and Mw of the silicon compound were calculated at 3,300 and 11,000,000, respectively, and a large peak was observed in the polymer region corresponding to a retention time of 6 to 10 minutes. Since the region is one wherein Mw is more than 400,000 and which is hard to determine, the Mw is expressed as ">1000000" which means greater than 1000000, and the Mw/Mn is expressed as ">200" which means greater than 200 in Table 1. Some monomers remained, but the molecular weight of the polymer was increased. The fact suggests that the hydrolytic copolycondensation of the starting monomers did not uniformly proceed.

The silicon compound obtained in Comparative Example 4 was dissolved in the same amount of PGMEA, and they were heated in an oil bath at a temperature of 60° C. to observe the appearance over time. Gelation was occurred on day 4.

Comparative Example 5

27.89 g (0.1 mol) of TMSOX, 28.84 g (0.185 mol) of TMOS, and 27.69 g of 1-propanol were charged into a reaction vessel provided with a stirrer and a thermometer, and then the mixed solution was heated to a temperature of 60° C. A mixed solution of 7.3 g of an aqueous solution of 25% by weight of tetramethylammonium hydroxide (containing 20 mmol of tetramethylammonium hydroxide), 18.53 g (1 mol) of water, and 17.75 g of 1-propanol was gradually added dropwise. Gelation occurred immediately after the addition. The fact suggests that gelation could not be prevented if the first and second processes are not separated in the production method.

Results of Examples and Comparative Examples are shown in Table 1. In Table 1, the symbol "-" means not performed or not measured.

The "solvent" in the first process means a solvent used for the alcohol exchange in the first process. Since the first process was not independently carried out in Comparative Example 5, the symbol "-" was entered. The "C concentration" in the second process refers to the percentage which is calculated from the amounts of the starting monomers (A) and (B) and where the calculated weight of the silicon compound (C) on the assumption that it is completely hydrolyzed and condensed in the second process is divided by the total weight of the charging monomers (A) and (B) in the second process. When the monomers are completely hydrolyzed and condensed, the hydrolytic polycondensation produces $SiO_2$ from the silicon compound having four siloxane bond-forming groups (Q monomer), $SiO_{1.5}$ from the silicon compound having three hydrolyzable groups (T monomer), and $SiO_1$ from the silicon compound having two hydrolyzable groups (D monomer).

TABLE 1

| | First process | | Second process | | | Compound C or condensate obtained | | | | |
|---|---|---|---|---|---|---|---|---|---|---|
| | Solvent | Reaction temp. | C Concentration | Reaction temp. | Gelation, etc. | Residual alkoxy | Yield/ % | Mn | Mw | Mw/Mn |
| Example 1 | 1-propanol | 60 | 25 | 60 | None | 0.8 | 91 | 3200 | 350,000 | 108 |
| Example 2 | 1-propanol | 60 | 15 | 60 | None | 0.9 | 90 | 3500 | 400,000 | 114 |
| Example 3 | 1-propanol | 20 | 15 | 20 | None | 2.0 | 85 | 3800 | 500,000 | 132 |
| Comparative Example 1 | Methanol | 21 | 25 | 20 | Gelation during reaction | — | — | — | — | — |
| Comparative Example 2 | Methanol | 60 | 25 | 60 | Poor separation of liquids | — | — | 5000 | >1,000,000 | >200 |
| Comparative Example 3 | Ethanol | 60 | 25 | 60 | Gelation on the next day | 2.6 | 91 | 4300 | >1,000,000 | >200 |
| Comparative Example 4 | 2-propanol | 60 | 25 | 60 | Gelation on day 4 | — | 90 | 3300 | >1,000,000 | >200 |
| Comparative Example 5 | — | — | 25 | 60 | Gelation during reaction | — | — | — | — | — |

[2] Evaluation of Physical Properties

For the silicon compound (C) produced without causing gelation in the above-described production of the silicon compound was measured and calculated for the yield (%) of the silicon compound and the content of residual alkoxy groups (%) in the following manner.

The yield (%) was calculated by the formula: (Isolated yield of the compound C)/(theoretical yield on the assumption that all the alkoxysilane of the Q monomer is converted to $SiO_2$, all the alkoxysilane of the T monomer is converted to $SiO_{1.5}$, and all the alkoxysilane of the D monomer is converted to $SiO_1$)×100. The content of the residual alkoxy groups (%) was calculated from the spectrum of $^1$H-NMR (nuclear magnetic resonance spectrum). Among Examples 1 to 3, in Examples 1 and 2 wherein the reaction temperature in the second process was high, the contents of the residual alkoxy groups were less than 1%, indicating very good results.

[3] Evaluation of Stability

The above-described silicon compound was evaluated for stability. The compound C obtained in Examples and the compound C obtained in Comparative Examples 3 and 4 were separately dissolved in equal amounts of PGMEA, and 2 ml of the solutions was placed in 5-ml glass tubes and tightly closed, and stored in an air thermostat bath at a temperature of 60° C. to observe the appearance over time. When the liquid did not flow in a sample tube upside down, the sample was regarded as gelated. The product obtained in Comparative Example 3 caused gelation on day 1, and that obtained in Comparative Example 4 caused gelation on day 4, while the product obtained in Examples did not cause gelation even after a lapse of 5 days.

[4] Evaluation of Molecular Weight

The ratio Mw/Mn is usually a value named as "polydispersity index". It is understood that when all the molecules are identical, Mw/Mn is 1, and that Mw/Mn is regarded as an index which becomes larger as the molecular weight distribution increases. Mw/Mn was less than 200 in Examples 1 to 3, the, however, Mw/Mn was more than 200 in Comparative Examples 2 to 4 wherein gelation did not occur during reaction. This is likely due to that, the reactivity of the monomers was equalized through the first process in Examples 1 to 3, whereby the molecular weight of the compound C was equalized. The reason why Example 1 showed the smallest Mw/Mn value of 108 is likely as follows: in the second process, the reaction was conducted at an initial concentration so as to obtain the C concentration of 25% and the reaction temperature of as high as 60° C., so that alcohol exchange reaction and alcoholysis reaction actively occurred concurrently with the condensation reaction, which resulted in a more uniform molecular weight distribution.

INDUSTRIAL APPLICABILITY

The silicon compound obtained by the present production method is solvent-soluble and is useful as a coating material having good storage stability. In addition, the compound has cationic curability, and thus is easily applied to the surface of various base materials, objects and the like. The cured product of the silicon compound has a high surface hardness, and thus is useful as a hard coat, a protective film for various base materials, or a resist film.

What is claimed is:

1. A method for producing a silicon compound (C), comprising a first process in which a silicon compound (A) represented by the following general formula (1) and a silicon compound (B) represented by the following general formula (2) are separately subjected to an alcohol exchange reaction in 1-propanol, and a second process in which hydrolytic copolycondensation is conducted under an alkaline condition, at a ratio of 0.3 to 2.8 mol of said silicon compound (A) based on 1 mol of said silicon compound (B)

$$SiX_4 \quad (1)$$

wherein the formula (1), X is a siloxane bond-forming group, and Xs may be the same or different from each other

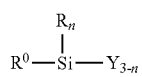

(2)

wherein the formula (2), $R^0$ is an organic group having an oxetanyl group, R is an alkyl group having 1 to 6 carbon atoms, an aralkyl group having 7 to 10 carbon atoms, an aryl group having 6 to 10 carbon atoms, or an organic group having an oxetanyl group, Y is a hydrolyzable group, Ys may be the same or different from each other, and n is 0 or 1.

2. The method for producing the silicon compound (C) according to claim 1, wherein $R^0$ in the formula (2) is an organic group represented by the following formula (3)

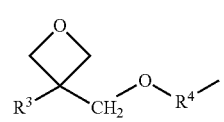

(3)

wherein the formula (3), $R^3$ is a hydrogen atom or an alkyl group having 1 to 6 carbon atoms, and $R^4$ is an alkylene group having 2 to 6 carbon atoms.

3. The method for producing the silicon compound (C) according to claim 2, wherein the amount of said alkaline agent for carrying out said second process under alkaline condition is in the range from 1 to 20 mol based on 100 mol of the total mol number of said silicon compound (A) and said silicon compound (B).

4. The method for producing the silicon compound (C) according to claim 3, wherein an alkaline agent for controlling the alkaline condition is a tetraalkylammonium hydroxide.

5. The method for producing the silicon compound (C) according to claim 3, wherein the initial concentration of a silicon monomer in said second process is in the range from 10% to 40% by weight, in terms of the concentration based on a weight of said silicon compound (C) to be formed.

6. The method for producing the silicon compound (C) according to claim 3, wherein the reaction temperature in said second process is in the range from 40° C. to 100° C.

7. The method for producing the silicon compound (C) according to claim 2, wherein the initial concentration of a silicon monomer in said second process is in the range from 10% to 40% by weight, in terms of the concentration based on a weight of said silicon compound (C) to be formed.

8. The method for producing the silicon compound (C) according to claim 2, wherein the reaction temperature in said second process is in the range from 40° C. to 100° C.

9. The method for producing the silicon compound (C) according to claim 2, wherein Y in the formula (2) is an alkoxy group, a cycloalkoxy group, or a aryloxy group.

10. The method for producing the silicon compound (C) according to claim 9, wherein the amount of said alkaline agent for carrying out said second process under alkaline condition is in the range from 1 to 20 mol based on 100 mol of the total mol number of said silicon compound (A) and said silicon compound (B).

11. The method for producing the silicon compound (C) according to claim 10, wherein an alkaline agent for controlling the alkaline condition is a tetraalkylammonium hydroxide.

* * * * *